United States Patent
Sabes et al.

(10) Patent No.: US 11,596,797 B2
(45) Date of Patent: Mar. 7, 2023

(54) REMOVAL OF STIMULATION ARTIFACT IN MULTI-CHANNEL NEURAL RECORDINGS

(71) Applicant: The Regents of the University of California, Oakland, CA (US)

(72) Inventors: Philip Sabes, San Francisco, CA (US); Joseph O'Doherty, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/494,246

(22) PCT Filed: Mar. 14, 2018

(86) PCT No.: PCT/US2018/022457
§ 371 (c)(1),
(2) Date: Sep. 13, 2019

(87) PCT Pub. No.: WO2018/170141
PCT Pub. Date: Sep. 20, 2018

(65) Prior Publication Data
US 2020/0129766 A1    Apr. 30, 2020

Related U.S. Application Data

(60) Provisional application No. 62/471,803, filed on Mar. 15, 2017.

(51) Int. Cl.
*A61N 1/36* (2006.01)
*A61F 2/72* (2006.01)
(Continued)

(52) U.S. Cl.
CPC ............ *A61N 1/36135* (2013.01); *A61B 5/24* (2021.01); *A61F 2/72* (2013.01); *A61N 1/025* (2013.01);
(Continued)

(58) Field of Classification Search
CPC .. A61N 1/025; A61N 1/0534; A61N 1/36053; A61N 1/36064; A61N 1/36067; A61N 1/36096; A61N 1/36135
See application file for complete search history.

(56) References Cited

U.S. PATENT DOCUMENTS 7,447,549 B2    11/2008   Litvak et al.
9,044,155 B2     6/2015   Strahl
(Continued)

FOREIGN PATENT DOCUMENTS

JP    2001-120511 A    5/2001

OTHER PUBLICATIONS

Trebaul et al. "Stimulation artifact correction method for estimation of early cortico-cortical evoked potentials". Journal of Neuroscience Methods 264 (2016) 94-102.*
(Continued)

*Primary Examiner* — Allen Porter
(74) *Attorney, Agent, or Firm* — Brian E. Davy; Bozicevic, Field & Francis LLP (57) ABSTRACT

Stimulation of nervous system components by electrodes can be used in many applications, including in the operation of brain-machine interfaces, bidirectional neural interfaces, and neuroprosthetics. The optimal operation of such systems requires a means of accurately measuring neural responses to such stimulations. However, currently the measurement of neural responses is difficult due to heavy stimulation artifacts arising from stimulatory pulses. The invention encompasses novel methods of estimating stimulation artifacts in measurements attained by recording electrodes and the effective removal of these artifacts. This provides improved neural recording systems and enables the deployment of closed-loop neural stimulation systems.

5 Claims, 8 Drawing Sheets

(51) Int. Cl.
*A61N 1/02* (2006.01)
*A61N 1/05* (2006.01)
*A61B 5/24* (2021.01)

(52) U.S. Cl.
CPC ....... *A61N 1/0534* (2013.01); *A61N 1/36053* (2013.01); *A61N 1/36064* (2013.01); *A61N 1/36067* (2013.01); *A61N 1/36096* (2013.01)

(56) References Cited

U.S. PATENT DOCUMENTS

2009/0177247 A1    7/2009   Neal et al.
2015/0018897 A1*   1/2015   Laudanski ............. A61N 1/025
                                                                                        607/57

OTHER PUBLICATIONS

Chernyy et al. "Time dependence of stimulation/recording-artifact transfer function estimates for neural interface systems". 31st Annual International Conference of the IEEE EMBS Minneapolis, Minnesota, USA, Sep. 2-6, 2009.*

Basir-Kazeruni et al. "A blind adaptive stimulation artifact rejection (ASAR) engine for closed-loop implantable neuromodulation systems". 8th International IEEE EMBS Conference on Neural Engineering Shanghai, China, May 25-28, 2017.*

O'Shea et al. "ERAASR: an algorithm for removing electrical stimulation artifacts from multielectrode array recordings" 2018 J. Neural Eng. 15 026020.*

Adib, Mani, and Edmond Cretu. "Wavelet-based artifact identification and separation technique for EEG signals during galvanic vestibular stimulation." Computational and mathematical methods in medicine vol. 2013 (2013): 167069. doi:10.1155/2013/167069.*

Al-Ani, T. et al., Automatic removal of high-amplitude stimulus artefact from neuronal signal recorded in the subthalamic nucleus, Journal of Neuroscience Methods, 2011, vol. 198, Issue 1, pp. 135-146. See the whole document.

International corresponding application, PCT/US18/022457, search report and written opinion dated Jun. 29, 2018.

Kohli et al., 2015. "Removal of Transcranial AC Current Stimulation Artifact From Simultaeneous EEG Recordings by Superposition of Moving Averages" 2015 37th Annual International Conference of the IEEE Engineering in Medicine and Biology Society, IEEE pp. 3436-3439. Published Aug. 25, 2015. Whole document.

Medrela et al., 2016. "A bidirectional neural interface circuit with active stimulation artifact cancellation and cross-channel common-mod noise suppression" IEEE Journal of Solid State Cirtcuits 51: 955-965, Published Apr. 1, 2016. Whole document.

* cited by examiner

REMOVAL OF STIMULATION ARTIFACT IN MULTI-CHANNEL NEURAL RECORDINGS

CROSS-REFERENCE TO RELATED APPLICATIONS

This application claims the benefit of priority to U.S. Provisional Application Ser. No. 62/471,803 entitled "Removing electrical stimulation artifacts from multi-channel electrical recordings," filed Mar. 15, 2017, the contents which are hereby incorporated by reference.

STATEMENT REGARDING FEDERALLY SPONSORED RESEARCH OR DEVELOPMENT

This invention was made with government support under grant no. W911NF-14-2-0043 awarded by the United States Army Research Laboratory's Army Research Office, and grant no. W81XWH-14-1-0510 awarded by the United States Army Medical Research and Materiel Command. The government has certain rights in the invention.

BACKGROUND OF THE INVENTION

Electrical stimulation of the nervous system is a powerful tool for addressing basic neuroscience questions, for various neurological therapies, and for the operation of brain-machine interfaces. Stimulation has been used to causally perturb neural circuits, for clinical diagnosis, for the treatment of nervous system disorders, and for restoring motor and sensory functions. Significant efforts are underway to develop bidirectional neural interfaces, the successful implementation of which will enable the development of next-generation neuroprosthetics.

In these systems, one or more stimulatory electrodes are activated, delivering a signal comprising a voltage or current pulse to a neural target, inducing neural responses. An array of recording electrodes may be utilized to capture neural signals generated in response to the stimulus pulse. However, successful measurement of the response signals is hampered by what is known as stimulation artifact, wherein the propagating stimulation signal is captured by electrodes of the recording array. This stimulation artifact can be of sufficient magnitude to obscure neural signals generated by the stimulation pulse. These voltage transients obscure neural activity for tens or even hundreds of milliseconds. The problem is exacerbated in high pulse rate stimulation, employed by many clinical applications, because an increasing fraction of the recording becomes contaminated by stimulation artifact as the pulse rate increases. Accordingly, the contaminating stimulation artifact must be removed if neural response signals are to be effectively measured.

Therefore, there is a great need for methods and technologies that permit neural recordings to be made without interference from simultaneous stimulations. While stimulation artifact amplitude and duration can be reduced through careful engineering of the stimulator, recording system, and delivery protocols, its production is an inevitable consequence of injecting electrical current into a volume of tissue.

Blanking may be used to reduce stimulation artifact. In blanking, recording amplifiers are taken off line during and immediately after delivery of a stimulation pulse. While this removes artifact, it is of limited practical use as it also results in total loss of signals during the blanking interval.

Another approach is to attempt to model stimulation artifact and then remove it post-hoc from measured signals. A common approach to stimulation artifact modeling is template subtraction. In template subtraction methods, a template of the expected stimulation artifact is generated by averaging the response to each stimulation pulse in contaminated recordings and then subsequently subtracting the average value from measured signals. Exemplary template methods are described by Wichmann, "A digital averaging method for removal of stimulus artifacts in neurophysiologic experiments." *Journal of Neuroscience Methods*, vol. 98, no. 1, pp. 57-62, 2000, and by Hashimoto at al., "A template subtraction method for stimulus artifact removal in high-frequency deep brain stimulation." *Journal of Neuroscience Methods*, vol. 113, no. 2, pp. 181-186, 2002.

However, template subtraction can be fairly unreliable as it assumes that the stimulation artifact does not vary across pulses. In practice, stimulation artifact will vary considerably across pulses of different intensities, pulse widths, and sites of stimulation. Even with these stimulation parameters held constant, template subtraction is often unable to completely remove the stimulation artifact during the pulsing interval. This makes it unsuitable for many closed-loop applications where stimulation parameters are tuned based on physiological responses. Additionally, template subtraction requires a high degree of temporal synchronization between the stimulator and the subtraction stage (or, equivalently, a high sampling rate for frequency domain subtraction). Finally, template subtraction can be unsuitable for multichannel stimulation paradigms because of complex overlapping stimulation artifacts.

Accordingly, there remains a need in the art for novel methods of accurately estimating and removing stimulation artifact in neural recordings.

SUMMARY OF THE INVENTION

Provided herein are various inventions that enable the accurate measurement of stimulation artifact and its removal from neural signals, yielding an effective measurement of neural response to stimulatory pulses. The invention is takes advantage of the novel observation that artifact signals are similar, i.e. statistically interdependent, across the channels of the array. Response signals, meanwhile, are generally observed only on a single electrode. The shared artifact characteristics across the array, and the large amplitude of artifact signals compared to response signals, allows the prediction of artifact contribution to measured signal on any selected electrode based on the mathematical relationship between signal artifact on the selected electrode and the other electrodes of the array In a first aspect, the scope of the invention encompasses novel methods of estimating stimulation artifacts in measurements attained by neural recording electrodes.

In a second aspect, the scope of the invention encompasses novel recording systems for measuring the response of various components of the nervous system to stimulatory pulses, wherein effective removal of stimulation artifacts is achieved.

In another aspect, the scope of the invention encompasses closed-loop systems and methods of operating such systems wherein neural responses can be accurately measured using the artifact removal methods of the invention. These clean measurements of neural response can then be utilized to guide the operation of closed-loop systems such as brain-machine interfaces, bidirectional neural interfaces, and neuroprosthetics.

DESCRIPTION OF THE DRAWINGS

FIG. 1. FIG. 1 is a schematic diagram depicting the elements of a neural recording system of the invention. The system comprises an array of implanted recording electrodes (104), implanted in a target structure (105) of the brain (101). Signals received from the electrodes are amplified by amplifiers (106, shown a single element although each electrode may have its own amplifier), passed through ADC elements (107, shown a single element although each electrode may have its own ADC) with ADC output to a processor (108) which calculates stimulation artifact and calculates artifact-removed neural response signals. Stimulatory pulses are applied to a responsive region of the brain (103) by one or more stimulation electrodes (102).

FIG. 2.

FIG. 3. FIG. 3 is a schematic diagram depicting the elements of a closed-loop system of the invention. The system comprises an array of implanted recording electrodes (304), implanted in a target structure (305) of the brain (301). Signals received from the electrodes are amplified by amplifiers (306, shown a single element although each electrode may have its own amplifier), passed through ADC elements (307, shown a single element although each electrode may have its own ADC) with ADC output to a processor (308) which calculates stimulation artifact and calculates artifact-removed neural response signals. Stimulatory pulses are applied to a responsive region of the brain (303) by one or more stimulation electrodes (302). The stimulation electrode(s) being under the control of a processor (309), which outputs control signals to an actuator (310). The actuator generates the stimulation pulses delivered by the one or more stimulation electrodes. In this closed loop system, the processor which calculates stimulation artifacts (308) outputs the corrected signal measurements to the processor (309) which controls the operation of the stimulation electrode(s). Processors 308 and 309 may be present as a single processor which performs the functions of both.

FIG. 4. FIG. 4 is a flow diagram depicting a general method of calculating neural response in a neural structure for each timepoint in a series of measurements attained from a recording array. Stimulatory pulses are delivered to a target neural structure (401) by one or more stimulation electrodes, and signals are measured in an array of recording electrodes (402). In an initial, side process, data generated by the process of 401 and 402 over several timepoints is utilized to generate statistical models which relate individual electrode stimulation artifacts to signals measured on the other electrodes of the array (403). Subsequently, for each time point, these regressions are applied to measured signals on the electrodes of the array (404), generating an estimate of stimulation artifact for each electrode. The estimated signal artifact is subtracted from signal measured on each electrode of the recording array during the timepoint (405), resulting in an estimate of response signals, which signals are output to a processor (406) which controls the stimulation electrode(s). Based upon these inputs, the processor calculates pulse stimulation parameters (407), which are output to an actuator (408) which generates the signals. The process is repeated (409) over the course of the operational phase.

FIGS. 5A, 5B, 5C, and 5D. FIG. 5a shows that stimulation artifacts measured in an array of recording electrodes has a stereotyped shape with a size that varies across the recording array. FIG. 5b shows a single pair of well correlated recording electrodes, illustrating this effect. FIG. 5c shows the distribution of pairwise correlations across the entire recording array. FIG. 5d shows that the degree of correlation decreases as a function of distance between electrodes.

FIG. 6.

FIGS. 7A, 7B, and 7C.

DETAILED DESCRIPTION OF THE INVENTION

The various inventions disclosed herein are directed to addressing the problem of stimulation artifacts in the measurement of responses to neural stimulation.

Stimulation pulses delivered to a target in the brain or other component of the nervous system will often produce a neurological response in associated elements of the nervous system, i.e. a depolarization of specific neurons that are responding to electrical signals or biochemical phenomena induced by the stimulation. This response will be termed the "neural response" and it will comprise a signal.

As used herein, a "signal" means a measurable electrical phenomenon, for example a spike in voltage, current, electric field intensity, or other measurable electrical phenomenon. At any given timepoint, the signal will have a value, magnitude, intensity, or other property that may be measured. In some implementations, the timepoint comprises a specific point in time. In some implementations, the timepoint comprises a time interval. If measured over a time interval, the signal may comprise a dynamic trace or waveform, wherein a parameter of such waveform is used as a measure of the signal. For example, the signal measure may comprise a peak, a peak-to-peak measurement, an integrated area under a curve, a decay constant, etc.

The neural response signal is often obscured or contaminated by stimulation artifact, as known in the art. Stimulation artifact is signal attributable to applied stimulation pulses and is not generated by organic neural activity of the animal. Excitations by a stimulation electrode are typically current pulses in the range of 10-100 microamperes, with resulting stimulation artifacts in the range of tens of millivolts. Meanwhile, neural response signals are typically of small intensity, for example in the range of 10-100 µV, and are thus are easily obscured by stimulation artifacts.

In an array of recording electrodes, the stimulation artifact generated in response to a stimulating pulse will vary among the several recording electrodes of the array. However, the inventors of the present disclosure have made the novel observation that stimulation artifact varies in a predictable and correlated manner among the several recording electrodes of the array. For any given recording electrode in the recording electrode array, the stimulation artifact generated by a stimulation pulse will be highly correlated with the stimulation artifacts generated in the other electrodes of the array at the same timepoint. Unexpectedly, this correlation is stable across a varied range of stimulation pulse parameters, including intensity, duration, frequency, and location. Accordingly, for any single electrode in an array of recording electrodes, a mathematical function may be generated that accurately estimates the stimulation artifact for the selected electrode based on signals measured by the other electrodes within the array.

This discovery provides the art with a novel means of accurately estimating the value of stimulation artifact signals for any electrode within an array, allowing the stimulation artifact to be subtracted from the measured signal, revealing any underlying neurological responses. The several inventions disclosed herein are based on this novel discovery and are described in detail next.

System for Measuring Neural Responses. In a first aspect, the scope of the invention encompasses a system for measuring neural response signals in a neural structure. The system will comprise various hardware elements and computer-readable instructions which direct the novel signal processing operations disclosed herein.

In the present disclosure, reference will be made to neural structures. A "neural structure," as referred to herein, means a structure or region of the nervous system. Exemplary neural structures include the cerebral cortex, the visual cortex, the motor cortex, sensorimotor cortex, the somatosensory cortex, or any other components of the brain, spinal cord, central nervous system, or peripheral nervous system. Reference will be made to a target neural structure, which comprises a neural structure into which stimulatory pulses are delivered. Reference will be made to a responsive neural structure, which comprises a structure in which recording electrodes are placed and wherein stimulation artifacts resulting from the aforementioned stimulatory pulses are generated. In some embodiments, the target neural structure and the responsive neural structure are the same structure. In other embodiments, the the target neural structure and the responsive neural structure are located in proximity to one another such that stimulatory pulses applied to the target neural structure propagate to the responsive neural structure. As an example, the target neural structure may comprise the sensorimotor cortex and the responsive structure may comprise the motor cortex.

A first element of the system is an array of recording electrodes. A recording electrode, as used herein, comprises an implantable electrical conductor that is in electrical contact with and/or is implanted within a responsive neural structure. Exemplary electrodes may comprise microneedles, shanks, pads or other geometries known in the art. Electrodes may comprise any suitable material, for example, silicon-based materials, stainless steel, tungsten, platinum, platinum-iridium alloys, iridium oxide, titanium nitride, or polymeric materials such as parylene, polyimide, and poly(ethylenedioxythiophene).

The recording electrodes will be part of an electrode array, the array comprising a plurality of recording electrodes, i.e. two or more recording electrodes, in any arrangement. Typically, electrode arrays will be integrated into a single implantable assembly, for example, a number of electrodes connected to a common base plate structure. However, the scope of the invention encompasses any plurality of recording electrodes, including individually placed electrodes or multiple, separately implanted assemblies. Exemplary electrode assemblies may have 16, 32, 64, 96, 100, 128 or any other number of recording electrodes. Electrodes in an assembly will typically be arranged in a grid or like geometric pattern with regular spacing between them. For example, spacings of 100-500 µm are common. For example, the assembly may comprise a circular, rectangular, square, hexagonal, or other geometrical arrangement of electrodes. Exemplary electrode arrays include the Utah array, as known in the art, comprising a grid of silicon wires with metallized electrode tips. Another example of an electrode array is the Michigan array, as known in the art, which may comprise a flexible array of silicon microwires connected to a common base plate with active electronics integrated into the baseplate.

The electrode arrays may comprise one or more counter electrodes and/or reference electrodes.

A second element of the recoding system will be a plurality of amplifiers, wherein one or more amplifiers are in connection with each of the recording electrodes. Each of the one or more amplifiers receives and amplifies voltage or currents detected by its corresponding recording electrode, as known in the art.

A third element of the recording system is a plurality of analog-to-digital converters (ADCs) which are in connection with each recording electrode of the array and which convert amplified analog signals output from each of the recording electrodes to digital signals that can be readily transferred, stored, and processed, as known in the art.

A fourth element of the recording system is one or more data storage devices for storing the signals output from each ADC. The one or more storage devices may be local, e.g. present on a memory element integrated with or in direct electrical connection with the system, or may be remote, e.g. a remote or cloud server or other storage device in a network connection with the recording system.

A fifth element of the recording system is a processor device configured to perform the various novel operations of the invention. One function of the processor device is to derive stimulation artifact estimation functions, as described below. A second function of the processor device is to estimate individual electrode stimulation artifact signals, as set forth below. A third function of the processor device is to calculate artifact-free neural response signals, as set forth below. These functions are performed by the processor device, which may comprise a general purpose computer or microprocessor. The functions are enabled by computer-readable code stored on a non-transitory recording medium, wherein the computer readable code in combination with the processor performs the enumerated functions. In one embodiment, the scope of the invention encompasses a computer-readable medium tangibly embodying a program of computer-readable instructions executable by a digital processing apparatus to derive stimulation artifact predictive functions, to apply such functions to signal data to estimate stimulation artifact for individual electrodes, and to calculate artifact-corrected neural response signal values.

Figure 1:
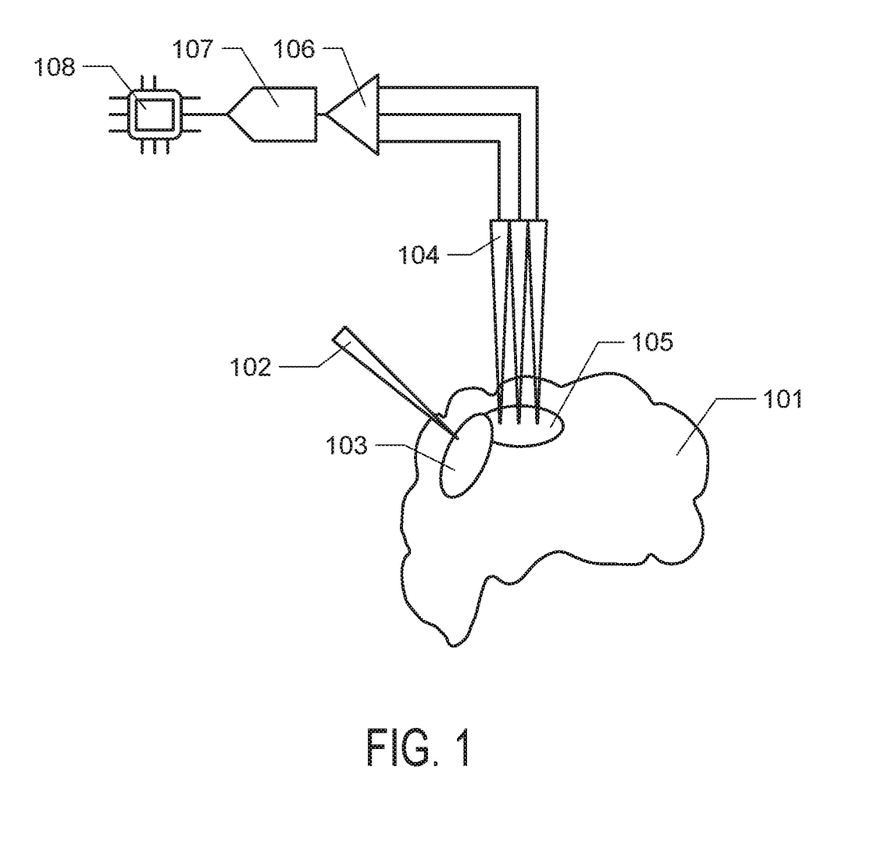
Figure 2:
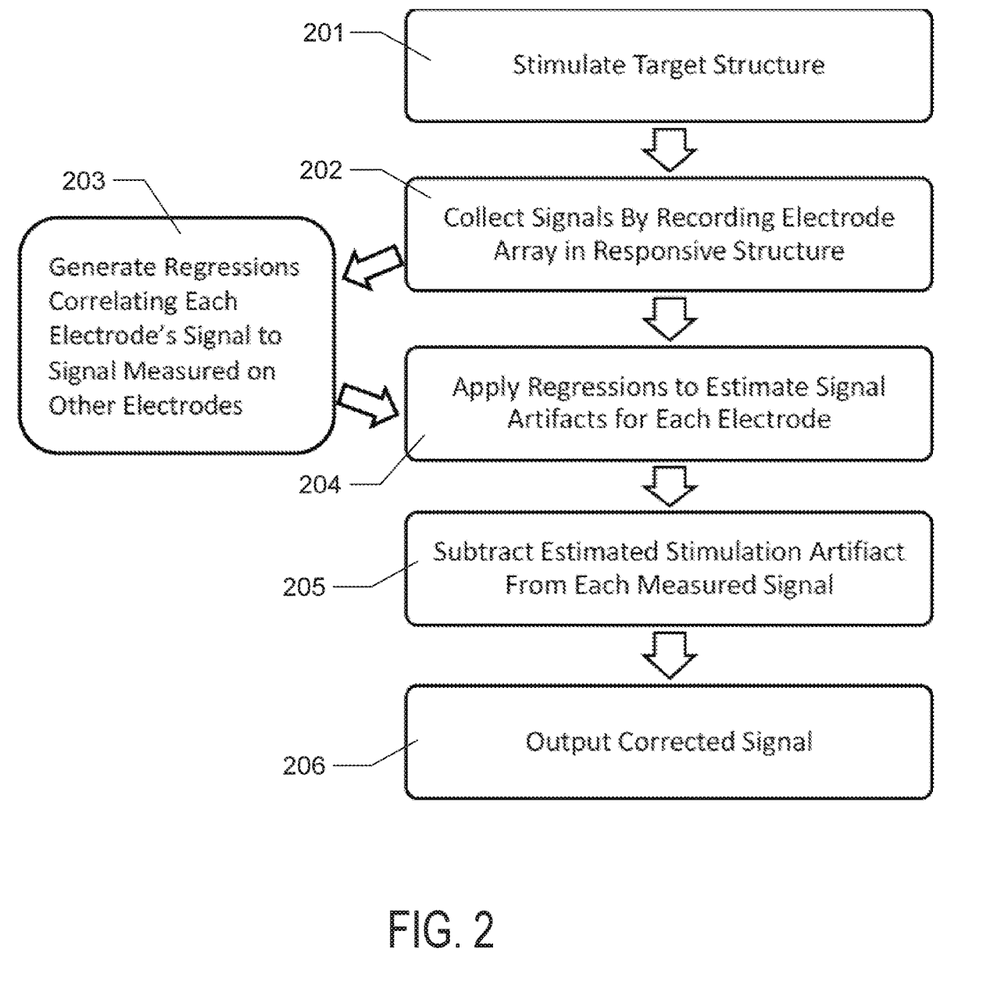
FIG. 2 is a flow diagram depicting a general method of calculating response signals in a neural structure for each timepoint in a series of measurements attained from a recording array. Stimulatory pulses are delivered to a target neural structure by one or more stimulation electrodes (201) and signals are measured in a responsive neural structure in an array of recording electrodes (202). In an initial, side process, data generated by the steps of 201 and 202 over several timepoints is utilized to generate statistical models which relate individual electrode stimulation artifacts to signals measured on the other electrodes of the array (203). Subsequently, for each timepoint, these calculated regressions are applied to measured signals on the electrodes of the array (204), generating an estimate of stimulation artifact for each electrode. The estimated signal artifact is subtracted from signal measured on each electrode of the recording array during the timepoint (205), resulting in an estimate of the artifact-corrected response signal for each electrode of the array, which can be output to a memory storage, processor, or other device.

The recording system will further comprise ancillary elements, including power supplies, wires, and other elements necessary for the function of the system. An exemplary recording system of the invention is depicted in FIG. 1. It will be understood that the depiction of the system in FIG. 1 is conceptual and that the system is not limited to any specific arrangement of elements or any specific hardware types. Elements presented as singular a may be deployed as multiple components that are functionally and/or electrically connected and elements presented as separate blocks may be implemented using a single multifunctional device.

The system may comprise, or may be operated in combination with, a neural stimulation system. The neural stimulation system will comprise one or more stimulation electrodes. A stimulation electrode is an electrode configured to deliver a stimulation pulse, i.e. an injection of voltage or current, for example, by capacitive or faradaic mechanisms, to a specific target neural structure. The stimulation electrodes may comprise any material known in the art, for example, titanium, titanium nitride, platinum, or iridium oxide. Like the recording electrodes, the stimulation electrodes may be present in an array, i.e. a number of electrodes connected to a common base structure which is implanted as a single unit. The stimulation electrodes will be in connection with voltage or current sources, for example, potentiometers. The stimulation pulses will be delivered under the control of a controller device, for example, a microcontroller that specifies stimulation pulse parameters such as intensity, pulse width, and frequency and the timing of pulse delivery.

In some embodiments, the neural stimulation system is configured separately from the recording system, e.g. in an open loop system. In some embodiments, the neural stimulation system is integrated with the recording system. For example, stimulation electrodes and recording electrodes may be integrated in separately implantable assemblies, or may be integrated in a single assembly. In some implementations, described below, the integrated stimulation and recording systems comprise a closed-loop system.

Stimulation Artifact Estimation and Removal. The systems of the invention are directed to the accurate measurement of neural response signals by novel methods of estimating and removing stimulation artifacts.

In one implementation, the invention encompasses a method of estimating the stimulation artifact signal on a selected recording electrode at a selected timepoint, wherein the selected recording electrode is one of an array, the array comprising a plurality of recording electrodes implanted in a responsive neural structure, the method comprising the steps of:
   recording a signal on each recording electrode of the array at the selected timepoint;
   inputting the recorded signals into a mathematical function, wherein the function outputs an estimated value for the stimulation artifact signal on the selected electrode;
   wherein the function utilizes the recorded signals measured for the electrodes of the array other than the selected electrode and a previously-established mathematical relationship between signal measured on the selected electrode and the signals measured on the other recording electrodes of the array.

This general method is based on the stable correlative relationship that exists between signal artifacts received on one electrode of the array and the signal artifacts received by the other recording electrodes of the array.

The mathematical relationship correlating each electrode's signal to signals measured on the other electrodes of the array can be derived using a subset of electrode array signal measurement data, e.g. a training set of data collected during operation of the system (for example, the initial data). In an alternative implementation, a set of training pulses is delivered, wherein signal is measured for each electrode in the array in response to a series of training stimulation pulses. The stimulation pulses of the training set may comprise pulse parameters (e.g. intensity, frequency) that will be utilized in the subsequent operational mode. The stimulation pulses of the training set may comprise a range of pulse parameters to increase the robustness of the mathematical relationships across different stimulation pulse parameters. The stimulation pulses of the training set may be delivered from a single stimulation electrode or a combination of multiple electrodes. The accuracy of the model will depend on utilizing a a sufficient number of samples in training the model to formulate the statistical interdependencies. For example, one minute of data sampled at 24.4 kHz recorded over 96 channels has been found sufficient in certain embodiments.

With respect to any selected recording electrode of the array, the mathematical relationship may comprise any predictive function based on signals measured on the other recording electrodes of the array. For example, the mathematical relationship may be derived by multiple linear regression, logistic regression analysis, linear discriminate analysis, partial least squares-discriminate analysis, multivariate non-linear regression, backwards stepwise regression, threshold-based methods, tree-based methods, Pearson's correlation coefficient, Support Vector Machine, generalized additive models, supervised and unsupervised learning models, cluster analysis, neural networks, and other predictive model-generating methods known in the art.

In one implementation, the result of the derivation step will be a series of mathematical formulae, each one directed to calculating predicted stimulation artifact for a particular electrode in the array based on the signals measured by the remainder of recording electrodes in the array.

In one embodiment, the estimation of stimulation artifact for a selected electrode is as in Equation 1:

$$\hat{X}_i(t) = \sum_{i \neq j} W_{ij} X_j(t). \qquad \text{Equation 1}$$

where $X_i(t)$ is the estimate of the stimulation artifact measured on electrode i at time t, $W_{ij}$ describes the contribution of the signal, $X_j(t)$, measured on each electrode j to that measured on electrode i. This procedure is repeated for all electrodes.

Thus, the artifact-free signal can be calculated through subtraction as in Equation 2:

$$X_{clean}(t) = X(t) - \hat{X}(t) \qquad \text{Equation 2.}$$

wherein Xclean(t) is the corrected signal with artifact signal removed at timepoint t.

In one implementation, a transformation matrix W can be fit to the recording array electrode signal data using standard linear regression. One simple approach is to iteratively regress the voltage on each channel, i, against the matrix of voltages on all other channels, j≠i, each regression producing a row in the matrix W. However, this approach is inefficient and does not scale well for large datasets.

Accordingly, in one embodiment, the multiple regressions are performed in a single computation that requires only one matrix inversion. In one embodiment the matrix, W is generated as in Equations 3-6:

$$W = -\Lambda Y, \text{ wherein,} \quad \text{Equation 3.}$$

$$Y \equiv (XX^T)^{-1}, \text{ and} \quad \text{Equation 4.}$$

$$\Lambda_{i,j} = \frac{\delta_{i,j}}{Y_{i,j}}, \quad \text{Equation 5.}$$

and wherein $$\delta_{i,j} = \begin{cases} 0 & \text{if } i \neq j \\ 1 & \text{if } i = j \end{cases}. \quad \text{Equation 6.}$$

wherein $\delta_{i,j}$ is the Kronecker delta function.

In related implementations, any matrix generation method may be utilized to develop a correction matrix W, wherein application of the matrix simultaneously calculates stimulation artifact across signals measured by all electrodes of the array based on the statistical interdependency of stimulation artifact signals across the array.

In practice, the strength of the correlations between artifacts received by any two electrodes depends on the geometry of the electrodes, the magnitude of the signals being measured and the frequency content of the signal. Closer electrodes, larger signals and lower frequencies are expected to be more highly correlated. Crucially, recording electrodes are, except for in specialized circumstances, placed with an inter-electrode spacing large enough that the physiological signals of interest are not measurable on multiple recoding electrodes of the array at the same time. As such, the only signals that can be measured on multiple channels simultaneously (i.e. large amplitude signals) are very likely to be stimulation artifacts, enabling the novel estimation methods of the invention.

The method of the invention is superior to blanking and template-based methods. Most advantageously, the method of the invention does not require the stimulation artifact to be temporally or spectrally distinct from the physiological signal of interest; does not make assumptions about the shape or size of the stimulation artifact or its relationship with stimulation parameters; is effective with noisy, unpredictable or otherwise time-varying stimulation artifacts; does not require temporal synchronization between the stimulator and the recording amplifier; and can accommodate multiple, simultaneous channels of stimulation with time-varying parameters.

In one embodiment, the array, comprising the selected plurality of electrodes used to calculate stimulation artifact for a selected recording electrode, comprises every recording electrode of an implanted assembly. In an alternative embodiment, the array comprises a selected subset of recording electrodes on the implanted assembly. For example, recording electrodes of the array that do not meet specified thresholds for predictive value may be omitted from the array used in stimulation artifact estimation. In another embodiment, in calculating the stimulation artifact for a selected electrode of an implant assembly, nearby recording electrodes are omitted from the plurality of electrodes comprising the array. For example, in the case of atypically closely-spaced recording electrodes, a neural response signal may be picked up by adjacent electrodes, which reduces the stimulation artifact predictive power of such nearby electrodes. Accordingly, in some implementations, djacent or nearby electrodes may be omitted from the set of recording electrodes used in stimulation artifact estimation.

The mathematical relationships used in calculating stimulation artifact may be dynamically refined during operation of the recording array, for example, by delivery of additional training pulses or using data gathered during the operational phase.

Figure 6:
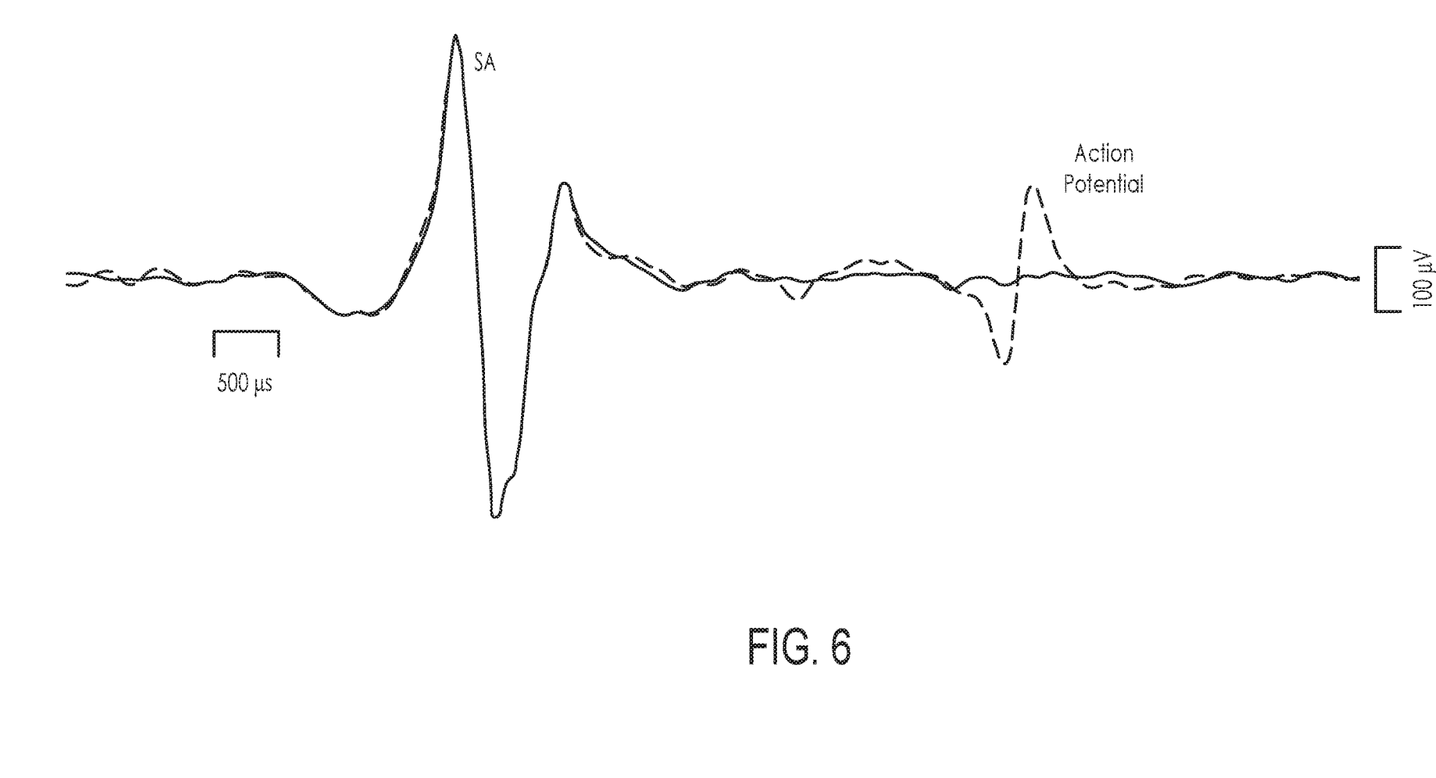
FIG. 6 depicts estimated stimulation artifact (solid line) and raw signal (dotted line) vs. time, with raw signal measured by a recording electrode within a recording array and the estimated stimulation artifact calculated by the methods of the invention. Peaks attributable to neural response are visible.
Figure 7A:
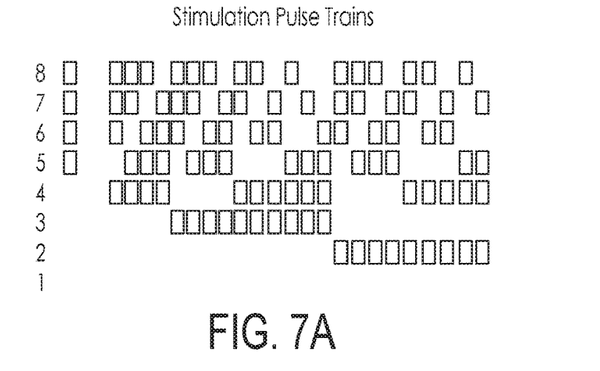
FIG. 7A depicts the sequence of stimulatory pulses delivered by an array of stimulatory electrodes to a target neural structure.
Figure 7B:
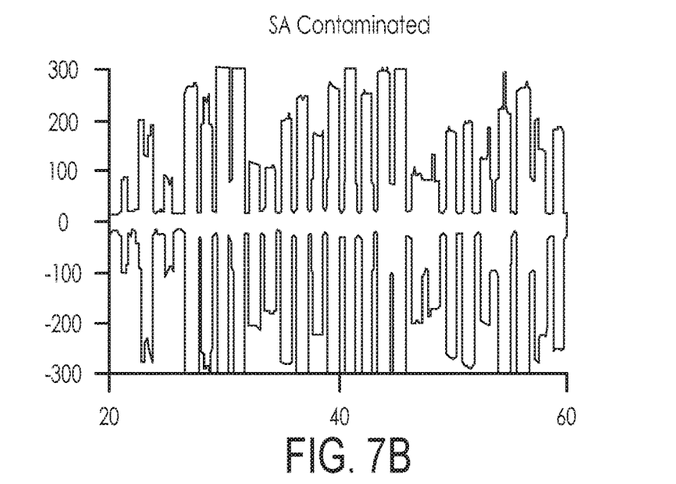
FIG. 7B depicts the raw, stimulation artifact-contaminated signal measured by a recording electrode in proximity to the stimulatory array.

Once stimulation artifact has been estimated for a selected electrode at a specific timepoint, the estimated stimulation artifact signal value is subtracted from the measured signal value for that timepoint, yielding a corrected signal value that represents the neural response signal, for example, as in Equation 2. Subtraction of the stimulation artifact may reveal neural response signals that were occluded by larger stimulation artifacts, for example as depicted in FIG. 6 and FIG. 7B. Advantageously, the methods of the invention do not affect the magnitude or shape of signals measured during non-stimulation intervals.

Closed-Loop Systems. In one implementation, the scope of the invention is directed to closed-loop neural interface systems. In normal physiology, movement, perception, and other functions mediated by the nervous system are guided by neural feedback, for example by sensory inputs and/or proprioceptive feedback. A major effort is underway to develop artificial, implantable systems which employ feedback-controlled stimulation to effect refined neural stimulations that echo natural feedback-guided processes. The successful development of such systems requires accurate measurement of neural responses. The novel methods of the invention enable the deployment of such systems by removing stimulation artifact and providing accurate decoding of neural responses.

Figure 3:
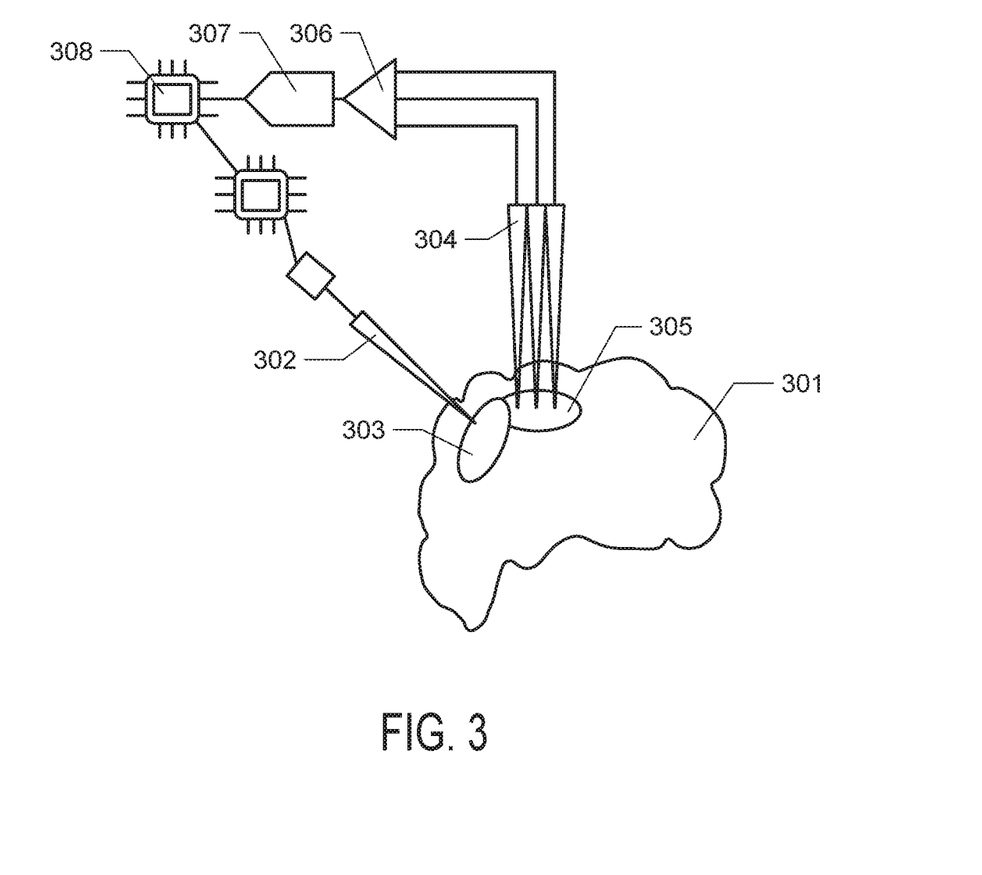

Accordingly, in one aspect, the scope of the invention encompasses a closed-loop system for feedback-guided neural stimulation. An exemplary embodiment of the closed-loop system is depicted in FIG. 3. The closed-loop system comprises a neural recording system, as described above, and a stimulation system. The closed loop system further comprises a connection between the processor means of the neural recording system and a controller device. The controller device comprises a processor which defines pulse delivery parameters and which also outputs control signals to an actuator. The actuator comprises a voltage or current source, for example comprising a potentiostat. The function of the actuator is to activate the stimulation electrodes as specified by the controller. In some embodiments, the processor device which performs the neural signal calculation is the same processor of the controller. Likewise, it will be understood that the depiction of the system in FIG. 3 is conceptual and that the system is not limited to any specific arrangement of elements or any specific hardware types. Elements presented as a single block may comprise multiple components that are functionally and/or electrically connected and elements presented as separate blocks may comprise a single multifunctional device.

The accurately measured neural responses enabled by the use of the invention are input to the controller element to guide the delivery of subsequent stimulation pulses. Such guidance can be implemented by use of a rule-based decision process, where pulse delivery parameters are determined in whole or in part as a function of measured neural responses.

The closed-loop system of the invention may comprise, for example, a brain machine interface, a neuroprosthesis, a bidirectional neural interface. For example, the closed-loop system may comprise a deep brain stimulation system, or a neuroprosthetic.

Figure 4:
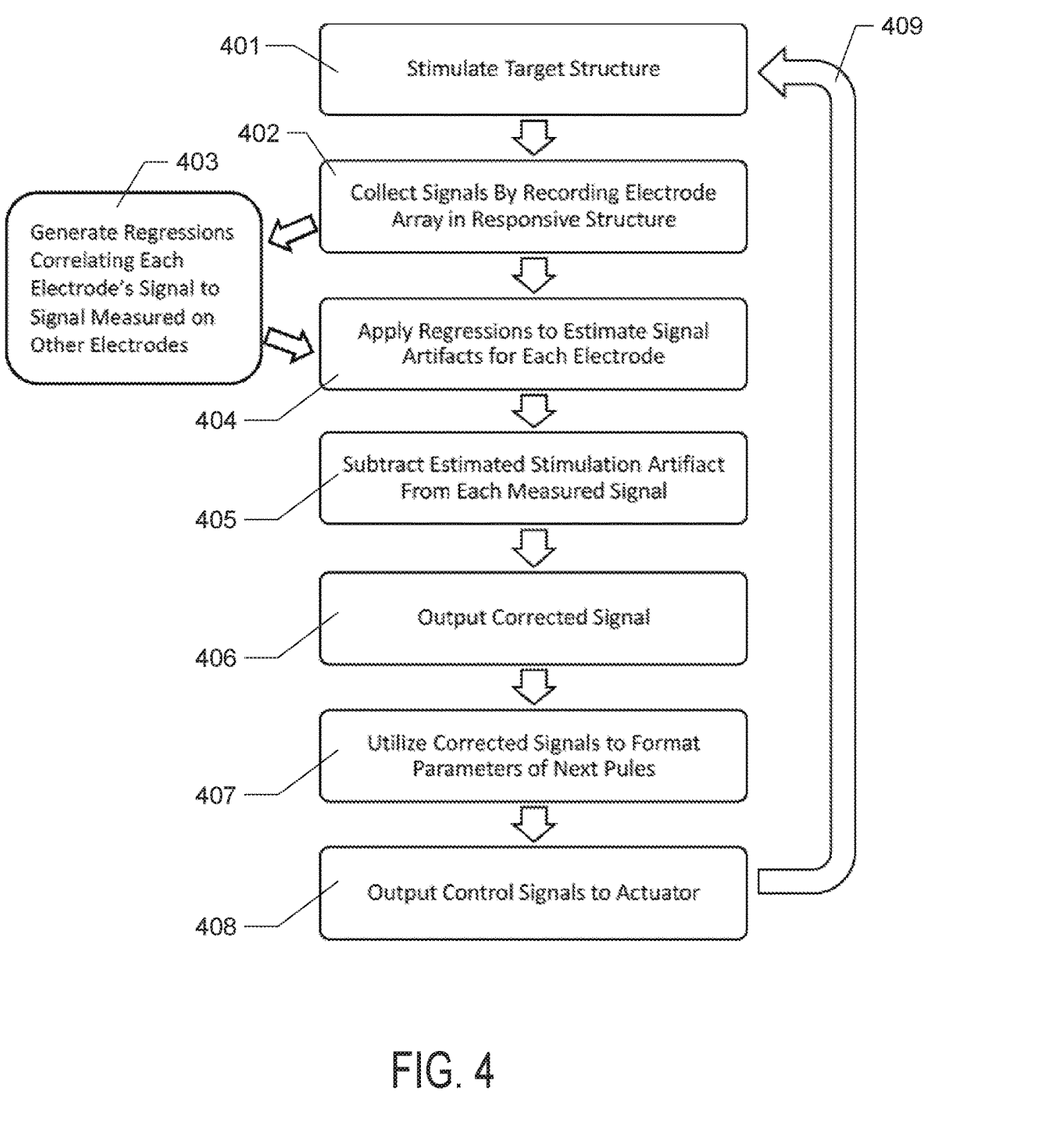

In one aspect, the scope of the invention encompasses a method of feedback-guided delivery of stimulation pulses to a target neural structure, for example as set forth in FIG. 4. In this method, the steps comprise:

delivering one or more stimulatory pulses to the target neural structure by means of one or more stimulation electrodes implanted therein, wherein the one or more stimulation electrodes are operated under the control of a controller device;

measuring one or more neural response signals in a responsive neural structure, comprising a neural structure that is responsive to stimulation of the target neural structure, by means of an array of recording electrodes implanted in the responsive neural structure;

calculating stimulation artifact-corrected neural response signals in the responsive neural structure by means of the method of claim 6;

inputting the calculated neural response signals to the controller device, wherein a rule-based decision process defines the parameters of subsequent pulse delivery to the target neural structure based on neural responses measured in the responsive neural structure; and delivering stimulatory pulses to the target neural structure according to the parameters determined by the rule-based process.

The process may be repeated continuously as necessary to achieve or maintain a desired outcome. For example, in one embodiment, the closed loop process is utilized to achieve a therapeutic outcome. In another embodiment, the closed loop process is utilized to achieve a task outcome, for example, movement of a limb, appendage, or prosthetic.

The method of operating closed-loop systems of the invention may be implemented in any relevant research or therapeutic context. For example, the the feedback-guided delivery of stimulatory pulses may implemented in a process selected from the group consisting of the following: cognitive control of a prosthetic device; proprioception-based guidance of a prosthetic or body part; vagus nerve stimulation for control of epilepsy; vagus nerve stimulation for control of depression; deep brain stimulation, for example, deep brain stimulation for controlling essential tremor; deep brain stimulation for controlling Parkinson's disease; deep brain stimulation for controlling dystonia; and deep brain stimulation for controlling depression.

It will be understood that the various systems and methods disclosed herein may be implemented in any animal species, including humans, for example, human patients in need of treatment, and in non-human animal species such as test animals or veterinary subjects. The systems and method may also be employed in explanted neural tissues and/or cultured neural cells.

EXAMPLES

Example 1

Stimulation Artifact Estimation and Removal

One adult male Rhesus macaque (Macaca mulatta), aged 11 years and weighing 12 kg, participated in this study. Two 96-channel silicon microelectrode arrays (Blackrock Microsystems, Salt Lake City, Utah) were chronically implanted into the left sensorimotor cortex. Each array consisted of 96, 10 mm long electrodes, spaced at 400 μm and covering a 4 mm by 4 mm area. One array, used for delivering stimulation, had tips coated with sputtered iridium oxide and was implanted over primary somatosensory cortex (Brodmann area 1, S1). The other, used for recording, had tips coated with Platinum and was implanted over primary motor cortex (Brodmann area 4, M1).

Electrical stimulation waveforms were delivered using an optically-isolated, computer-controlled stimulator (IZ2; Tucker-Davis Technologies, Alachua, Fla.). Symmetric, biphasic, cathode-leading, charge-balanced, square-wave "Lilly" waveforms were delivered, with an interphase interval imposed between the cathode and anode phases.

Recordings were made using an RZ2 BioAmp Processor with PZ2 Preamplifier (Tucker-Davis Technologies, Alachua, Fla.). The amplifier system had an input impedance of 100 kΩ, an input referred noise of 2 μV RMS, and a maximum voltage of ±10 mV, which permitted recording of stimulation artifact without amplifier saturation over a wide range of current intensities. After stimulation artifact removal and before spike detection, a causal IIR bandpass filter (4th order Butterworth; $F_{pass}$=500 Hz to 5000 Hz) was applied to emphasize spike band.

Figure 5A:
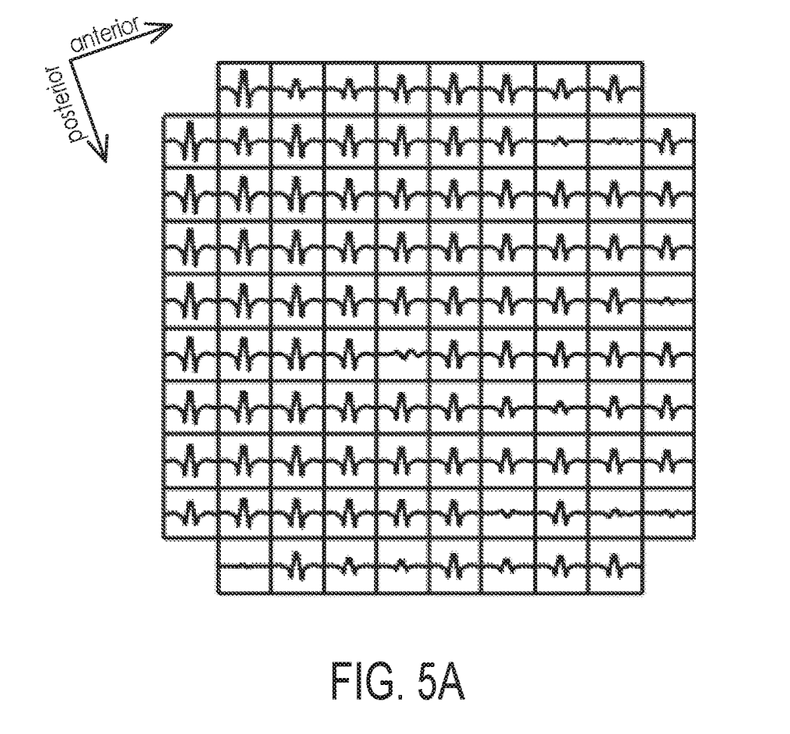
FIGS. 5A, 5B, 5C, and 5D depict correlated stimulation artifacts across an array of recording electrodes.
Figure 5B:
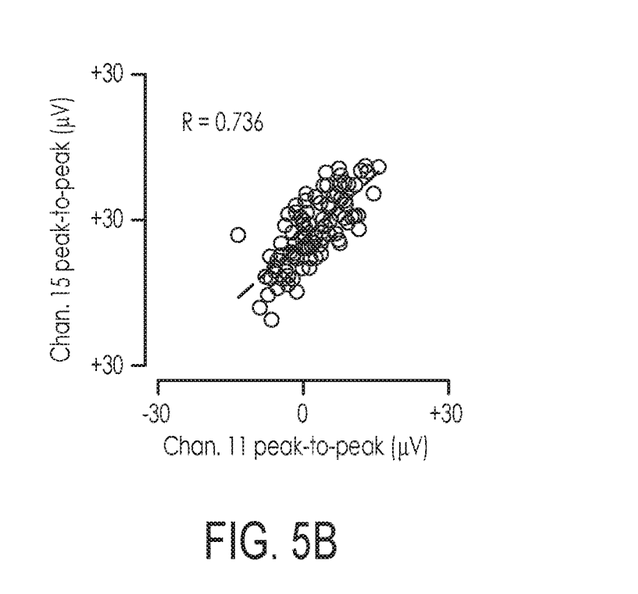
Figure 5C:
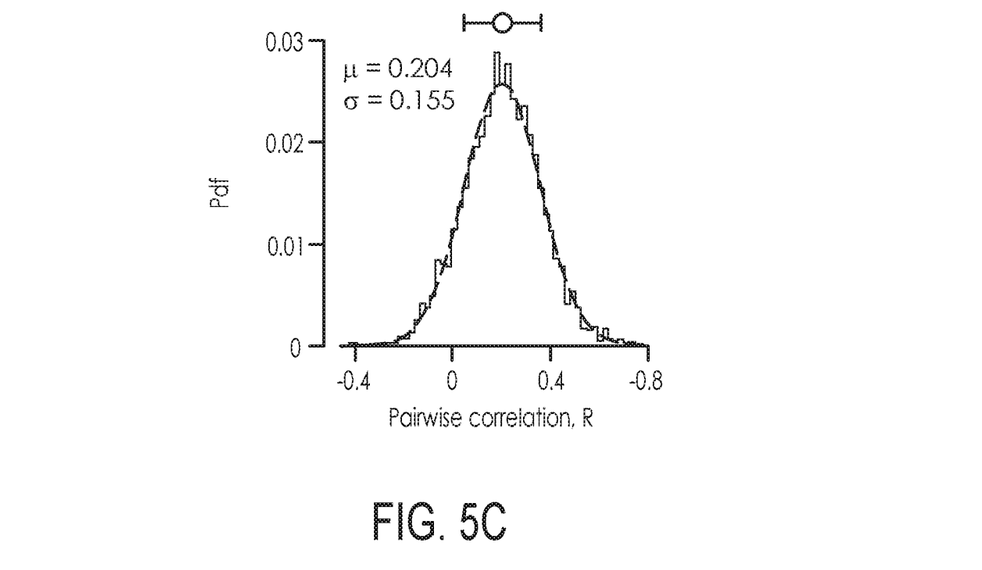
Figure 5D:
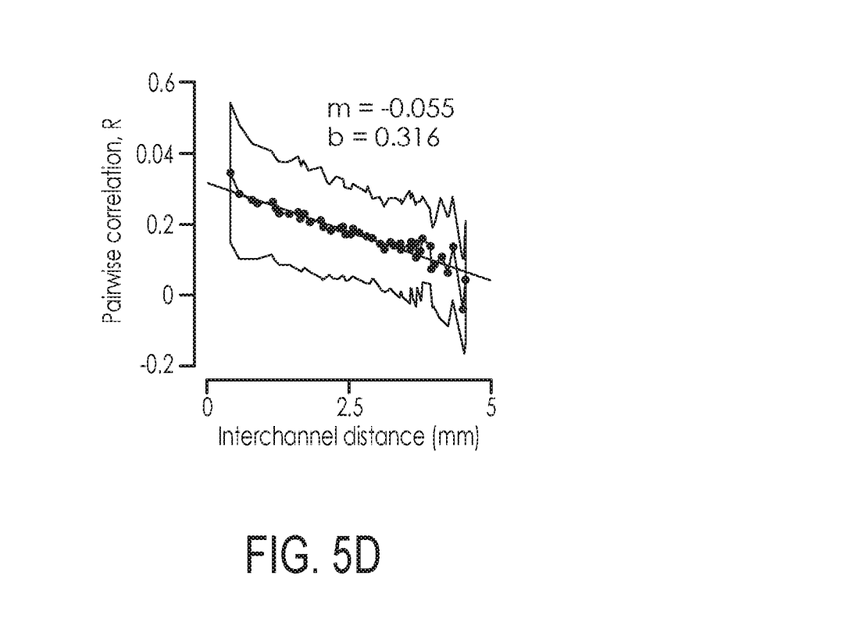

It was observed that the stimulation artifact has a stereotyped shape with a size that varied across the recording array (FIG. 5a); electrodes located farther away from the stimulation site had smaller stimulation artifact amplitudes. However, despite the generally stereotyped size and shape, there was pulse by pulse variability in stimulation artifact amplitude. This variability (on the order of μV) was much smaller than the absolute size of the stimulation artifact (on the order of mV), however it was still a significant fraction of the size of action potentials (also μV). This unexplained variability indicates why template subtraction is often not completely effective at eliminating SA Importantly, the pulse-by-pulse variability in stimulation artifact was correlated across recording channels. FIG. 5b shows a single pair of well correlated recording electrodes, illustrating this effect. FIG. 5c shows the distribution of pairwise correlations across the entire recording array; wherein the majority of electrode pairs had positive correlations. Pairwise correlation decreased linearly with inter-electrode spacing (FIG. 5d), but were on average positive even for the most distant pairs of electrodes.

The correlated variability in stimulation artifact amplitude observed across the recording array enabled development of a novel approach to improved stimulation artifact estimation: by using multiple observations of the SA, recorded on multiple different channels, moment by moment estimation of the stimulation artifact that would be observed on each other channel could be calculated.

The process of Equations 3-6 above was applied to determine stimulation artifact for each electrode in the array. These operations were derived as follows:

Signal data was formatted as an n×m matrix X, with the goal being to minimize SA, τ, as in Equation 7:

$$\mathcal{J}(A) = \sum_{i,j}\left(\left(\sum_k A_{i,k}X_{k,j}\right) - X_{i,j}\right)^2. \quad \text{Equation 7}$$

subject to A i,i=0, for all i. The goal is to make A a hollow matrix. Using the method of Lagrange multipliers, Equation 8 is applied:

$$\mathcal{L}(A, \lambda) = \sum_{i,j}\left(\left(\sum_k A_{i,k}X_{k,j}\right) - X_{i,j}\right)^2 + \sum_i \lambda_i A_{i,i}. \quad \text{Equation 8}$$

with the requirement of Equation 9:

$$\frac{\partial \mathcal{L}}{\partial \lambda_\alpha} = A_{\alpha,\alpha} = 0. \quad \text{Equation 9}$$

-continued and Equation 10:

$$\frac{\partial \mathcal{L}}{\partial A_{\alpha,\beta}} = 2\sum_{i,j}\left(\left(\left(\sum_k A_{i,k}X_{k,j}\right) - X_{i,j}\right)\left(\sum_k \delta_{i,\alpha}\delta_{k,\beta}X_{k,j}\right)\right) \cdot$$

$$\sum_i \lambda_i \delta_{i,\alpha}\delta_{i,\beta}$$

$$= 2\sum_j\left(\left(\left(\sum_k A_{\alpha,k}X_{k,j}\right) - X_{\alpha,j}\right)X_{\beta,j}\right) + \lambda_\alpha \delta_{\alpha,\beta}$$

$$= 2\sum_j\left(\left(\sum_k A_{\alpha,k}X_{k,j}\right)X_{j,\beta}^T - X_{\alpha,j}X_{j,\beta}^T\right) + \lambda_\alpha \delta_{\alpha,\beta}$$

$$= 0,$$

Equation 10 where $\delta_{\alpha,\beta}$ is the Kronecker delta function. From Equation 10, Equation 11 is derived:

$$AXX^T - XX^T = -\frac{1}{2}\Lambda \qquad \text{Equation 11.}$$

where $\Lambda_{\alpha,\beta} = \lambda_\alpha \delta_{\alpha,\beta}$. Assuming that XXT is full rank, the result is Equation 12:

$$A = I - \frac{1}{2}\Lambda Y \qquad \text{Equation 12.}$$

where $Y \equiv (XX^T)^{-1}$.

Figure 7C:
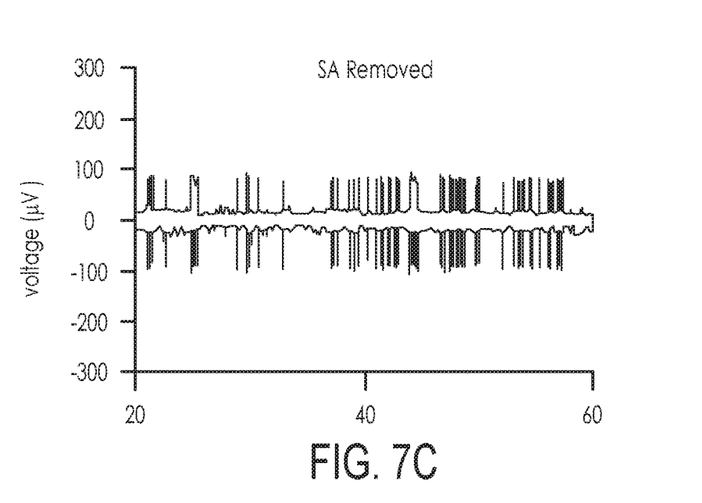
FIG. 7C depicts the artifact-corrected signal representing neural response peaks.

Subtraction of estimated stimulation artifact from raw signal for a single electrode, as depicted in FIGS. 7B and 7C, demonstrates the ability of the method to reveal neural responses that are obscured by stimulation artifact in uncorrected signals.

Example 2

Comparison of Stimulation Artifact Removal Methods

Electrodes chronically implanted in the primary somatosensory cortex of a rhesus macaque were used to deliver stimulatory pulses and signals were recorded by recording electrodes in the motor cortex. The methods of the invention were applied to estimate stimulation artifact. These methods were compared to two commonly employed stimulation artifact mitigation techniques: template subtraction and blanking (5 ms after each pulse). While blanking is of limited practical use, as it also rejects neural signals, it was included in the comparison to provide a baseline level of performance. The performance of the novel methods of the invention was superior to both template subtraction and blanking.

Stimulation was first achieved using single channels (that is, only one channel could be stimulating at a time) and the effectiveness of each stimulation artifact removal method was quantified as a function of neural acquisition sampling rate. The performance of template subtraction suffered at low sampling rates, highlighting a fundamental limitation of that method: its effectiveness is very sensitive to precise timing. In contrast, the method of the invention was effective across a range of data sampling rates. Next, stimulation was achieved on multiple channels simultaneously. This is challenging scenario for any stimulation artifact mitigation method. Template subtraction was again unable to completely remove the stimulation artifact, while the method of the invention remained effective.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of estimating, with a processor, a stimulation artifact signal on a selected recording electrode at a selected timepoint; wherein the stimulation artifact signal is a signal attributable to one or more stimulation pulses applied by one or more stimulation electrodes and is not a signal generated by organic neural activity, further wherein the selected recording electrode is one of an array, the array comprising a plurality of recording electrodes implanted in a neural structure, the method comprising the steps of:
   recording a signal on each recording electrode of the array at the selected timepoint;
   inputting the recorded signals into a mathematical function, wherein the mathematical function applies a previously-established correlative relationship between a signal artifact received by the selected recording electrode and signal artifacts received by all other recording electrodes of the array, and
   the correlative relationship having been derived using pulses previously delivered by the one more stimulation electrodes and signals resulting therefrom that were measured by the selected recording electrode and all other recording electrodes of the array:
   wherein the function outputs an estimated value for the stimulation artifact signal on the selected recording electrode;
   wherein the function is described as:

$$\hat{X}_i(t) = \sum_{i \neq j} W_{ij} X_j(t)$$

where X i(t) is the estimated value of the stimulation artifact on the selected electrode i at time t, Wij describes the previously-established correlative relationship, and Xj(t) is the signal recorded on respective electrode j selected from all the other recording electrodes of the array that are not selected recording electrode i:
   wherein the method further comprises:
   calculating an artifact-corrected signal for the selected recording electrode at the selected timepoint by subtracting the estimated stimulation artifact signal of the selected recording electrode from the signal measured by that recording electrode at the selected timepoint; and
   delivering subsequent electrode pulses by the one or more stimulation electrodes based on the calculated artifact-corrected signal.

2. The method of claim 1, wherein the neural structure is selected from the group consisting of the cerebral cortex, the visual cortex, the motor cortex, the somatosensory cortex, the sensimotor cortex, the spinal cord, or a component of the peripheral nervous system.

3. A closed-loop neural stimulation system, the closed loop neural stimulation system comprising:
   one or more stimulation electrodes, wherein operation of the one or more stimulation electrodes is controlled by a controller device;
   a system for calculating artifact-corrected neural response signals generated in response to one or more stimulation pulses delivered by the one or more stimulation electrodes, the system comprising:

an array, the array comprising a plurality of recording electrodes configured to be implanted in a neural structure;

a plurality of amplifiers, wherein one or more amplifiers is in connection with each recording electrode of the array;

a plurality of analog to digital converters, wherein each analog to digital converter is configured to convert recording electrode outputs to digital signals;

one or more signal storage devices capable of storing signals output by the plurality of analog to digital converters; and a processing device, the processing device configured to calculate artifact-corrected signals at a selected timepoint for each recording electrode in the array in response to one or more stimulation pulses delivered by the one or more stimulation electrodes, wherein the processing device is further configured to perform the steps of:

recording a signal on each recording electrode of the array at the selected timepoint;

inputting each of the recorded signals into a mathematical function, wherein the mathematical function applies a previously-established correlative relationship between a signal artifact received by the selected recording electrode and signal artifacts received by all other recording electrodes of the array, and the correlative relationship having been derived using pulses previously delivered by the one or more stimulation electrodes and signal artifacts received by all other recording electrodes of the array, and the correlative relationship having been derived using pulses previously delivered by the one more stimulation electrodes and signals resulting therefrom that were measured by the selected recording electrode and all other recording electrodes of the array;

wherein the function outputs an estimated value for the stimulation artifact signal on the selected recording electrode;

wherein the function is described as:

$$\hat{X}_i(t) = \sum_{i \neq j} W_{ij} X_j(t)$$

where $X_j(t)$ is the estimated value of the stimulation artifact on the selected electrode i at time t, $W_{ij}$ describes the previously-established correlative relationship, and $X_j(t)$ is the signal recorded on respective electrode j selected from all the other recording electrodes of the array that are not selected recording electrode i calculating an artifact-corrected signal for each electrode in the recording array at the selected timepoint by subtracting the estimated stimulation artifact of the selected recording electrode from the signal measured by that recording electrode at the selected timepoint; and wherein the processing device is configured to output the artifact-corrected signals of the recording electrodes in the array to the controller device; and wherein, based upon the artifact-corrected signal values received from the processor device, the controller is configured to determine parameters of stimulation pulses and cause the stimulation electrodes to deliver stimulation pulses according to the determined parameters.

4. The closed-loop neural stimulation system of claim 3, wherein
the closed-loop neural stimulation system comprises a brain-machine interface, a neuroprosthetic, or bidirectional neural interface.

5. The closed-loop neural stimulation system of claim 3, wherein
the closed-loop neural stimulation system is configured to perform a process selected from the group consisting of the following: cognitive control of a prosthetic device; proprioception-based guidance of a prosthetic or body part; vagus nerve stimulation for control of epilepsy; vagus nerve stimulation for control of depression; deep brain stimulation for controlling essential tremor; deep brain stimulation for controlling Parkinson's disease; deep brain stimulation for controlling dystonia; and deep brain stimulation for controlling depression.

* * * * *

UNITED STATES PATENT AND TRADEMARK OFFICE
CERTIFICATE OF CORRECTION

PATENT NO. : 11,596,797 B2
APPLICATION NO. : 16/494246
DATED : March 7, 2023
INVENTOR(S) : Philip N. Sabes et al.

It is certified that error appears in the above-identified patent and that said Letters Patent is hereby corrected as shown below:

On the Title Page

On Page 2, item (56), under "Other Publications" in Column 2, Line 17, delete "Simultaeneous" and insert -- Simultaneous --.

On Page 2, item (56), under "Other Publications" in Column 2, Line 23, delete "Cirtcuits" and insert -- Circuits --.

In the Specification

In Column 2, Line 46, delete "array" and insert -- array. --.

In Column 5, Line 50, delete "the the" and insert -- the --.

In Column 8, Line 14, delete "a a" and insert -- a --.

In Column 9, Line 63, delete "djacent" and insert -- adjacent --.

In Column 11, Line 31, delete "the the" and insert -- the --.

In Column 11, Line 61, delete "10" and insert -- 1.0 --.

In the Claims

In Column 14, Line 25, in Claim 1, delete "one more" and insert -- one or more --.

In Column 14, Line 28, in Claim 1, delete "array:" and insert -- array; --.

In Column 14, Line 38, in Claim 1, delete "X i(t)" and insert -- Xi(t) --.

Signed and Sealed this
Eighteenth Day of April, 2023

Katherine Kelly Vidal
*Director of the United States Patent and Trademark Office*

CERTIFICATE OF CORRECTION (continued)
U.S. Pat. No. 11,596,797 B2

In Column 14, Line 44, in Claim 1, delete "i:" and insert -- i; --.

In Column 15, Line 38, in Claim 3, delete "one more" and insert -- one or more --.

In Column 15, Line 41, in Claim 3, delete "array:" and insert -- array; --.

In Column 15, Line 44, in Claim 3, delete "electrode:" and insert -- electrode; --.

In Column 16, Line 7, in Claim 3, delete "X j(t)" and insert -- Xi(t) --.